US012385062B2

(12) United States Patent
Loiler

(10) Patent No.: US 12,385,062 B2
(45) Date of Patent: Aug. 12, 2025

(54) INCREASING TISSUE SPECIFIC GENE DELIVERY BY CAPSID MODIFICATION

(71) Applicant: RESEARCH INSTITUTE AT NATIONWIDE CHILDREN'S HOSPITAL, Columbus, OH (US)

(72) Inventor: Scott Allen Loiler, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 953 days.

(21) Appl. No.: 16/980,821

(22) PCT Filed: Mar. 14, 2019

(86) PCT No.: PCT/US2019/022353
§ 371 (c)(1),
(2) Date: Sep. 14, 2020

(87) PCT Pub. No.: WO2019/178412
PCT Pub. Date: Sep. 19, 2019

(65) Prior Publication Data
US 2021/0087584 A1    Mar. 25, 2021

Related U.S. Application Data

(60) Provisional application No. 62/644,317, filed on Mar. 16, 2018.

(51) Int. Cl.
*C12N 15/86* (2006.01)
*C07K 14/005* (2006.01)

(52) U.S. Cl.
CPC ............ *C12N 15/86* (2013.01); *C07K 14/005* (2013.01)

(58) Field of Classification Search
None
See application file for complete search history.

(56) References Cited

U.S. PATENT DOCUMENTS

| 2014/0056854 A1 | 2/2014 | Asokan et al. | |
| 2015/0023924 A1* | 1/2015 | High | C12N 15/86 435/456 |

FOREIGN PATENT DOCUMENTS

| CN | 105579465 A | 5/2016 | | |
| EP | 0 920 514 A1 | 6/1999 | | |
| JP | 2014-507145 A | 3/2014 | | |
| JP | 2016-525356 A | 8/2016 | | |
| WO | WO-2012/109570 A1 | 8/2012 | | |
| WO | WO-2013/158879 A1 | 10/2013 | | |
| WO | WO-2015/013313 A2 | 1/2015 | | |
| WO | WO-2015121501 A1 * | 8/2015 | ............ | A61K 48/00 |
| WO | WO-2017058892 A2 * | 4/2017 | ............ | A61P 25/00 |
| WO | WO-2017/181014 A1 | 10/2017 | | |
| WO | WO-2017/197355 A2 | 11/2017 | | |
| WO | WO-2019/178412 A1 | 9/2019 | | |
| WO | WO-2020/047472 A1 | 3/2020 | | |

OTHER PUBLICATIONS

Kyte J, Doolittle RF. A simple method for displaying the hydropathic character of a protein. J Mol Biol. May 5, 1982;157(1):105-32. doi: 10.1016/0022-2836(82)90515-0. PMID: 7108955. (Year: 1982).*
Partial Supplementary European Search Report dated Nov. 26, 2021, from application No. 19768552.2, 15 pages.
Extended European Search Report dated Apr. 26, 2022, from application No. 19768552.2.
Wang, et al., "Muscle stem cells at a glance", Journal of Cell Science, Nov. 1, 2014, vol. 127, pp. 4543-4546.
Asokan, A., et al., "Reengineering a receptor footprint of adeno-associated virus enables selective and systemic gene transfer to muscle", Nat Biotechnol, 2010. 28(1): p. 79-82.
DiMattia, M.A., et al., "Structural insight into the unique properties of adeno-associated virus serotype 9", J Virol, 2012. 86(12): p. 6947-6958.
Govindasamy, L., et al., "Structural insights into adeno-associated virus serotype 5", J Virol, 2013. 87(20): p. 11187-11199.
Grimm, D., et al., "In vitro and in vivo gene therapy vector evolution via multispecies interbreeding and retargeting of adeno-associated viruses", J Virol, 2008. 82(12): p. 5887-5911.
International Search Report and Written Opinion issued in PCT Application No. PCT/US2019/022353 dated Aug. 22, 2019, 12 pages.
Li, C. et al., "Single amino acid modification of adeno-associated virus capsid changes transduction and humoral immune profiles", J Virol, 2012. 86(15): p. 7752-7759.
Loiler, S.A., et al., Targeting recombinant adeno-associated virus vectors to enhance gene transfer to pancreatic islets and liver. Gene Ther, 2003. 10(18): p. 1551-8.
Pulicherla, N. et al., "Engineering liver-detargeted AAV9 vectors for cardiac and musculoskeletal gene transfer", Mol Ther, 2011. 19(6): p. 1070-1078.

(Continued)

*Primary Examiner* — Benjamin P Blumel
*Assistant Examiner* — Jeffrey Mark Sifford
(74) *Attorney, Agent, or Firm* — Foley & Lardner LLP

(57) ABSTRACT

Modified capsid proteins, isolated polynucleotides, methods for the preparation of modified capsid proteins, recombinant viral particles, recombinant expression systems for the generation of modified viral particles, and methods of gene editing and regulation are provided herein.

11 Claims, 3 Drawing Sheets
Specification includes a Sequence Listing.

(56) References Cited

OTHER PUBLICATIONS

Raupp, C. et al., "The threefold protrusions of adeno-associated virus type 8 are involved in cell surface targeting as well as postattachment processing", J Virol, 2012. 86(17): p. 9396-9408.
Bentzinger et al., "Cellular dynamics in the muscle satellite cell niche," EMBO Reports, 2013, 14(12), p. 1062-1072.
Bianconi et al., "An estimation of the number of cells in the human body," Annals of Human Biology, 2013, 40(6), pp. 463-471.
Fang et al., "Comparison of Adeno-Associated Virus Serotypes and Delivery Methods for Cardiac Gene Transfer," Human Gene Therapy Methods, 2012, 23(4), pp. 234-241.
Mori et al., "Biodistribution of a Low Dose of Intravenously Administered AAV-2, 10, and 11 Vectors to Cynomolgus Monkeys," Jpn J Infect Dis, 2006, 59(5), p. 285-293.
Tran, et al., "Laminin drives survival signals to promote a contractile smooth muscle phenotype and airway hyperreactivity," FASEB J, 2013, 27(10), pp. 3991-4003.
Xie Qing, et al., "The atomic structure of adeno-associated virus (AAV-2), a vector for human gene therapy," Proc Natl Acad Sci USA, 2002, vol. 99, No. 16, pp. 10405-10410.

\* cited by examiner

FIGS. 1A-E
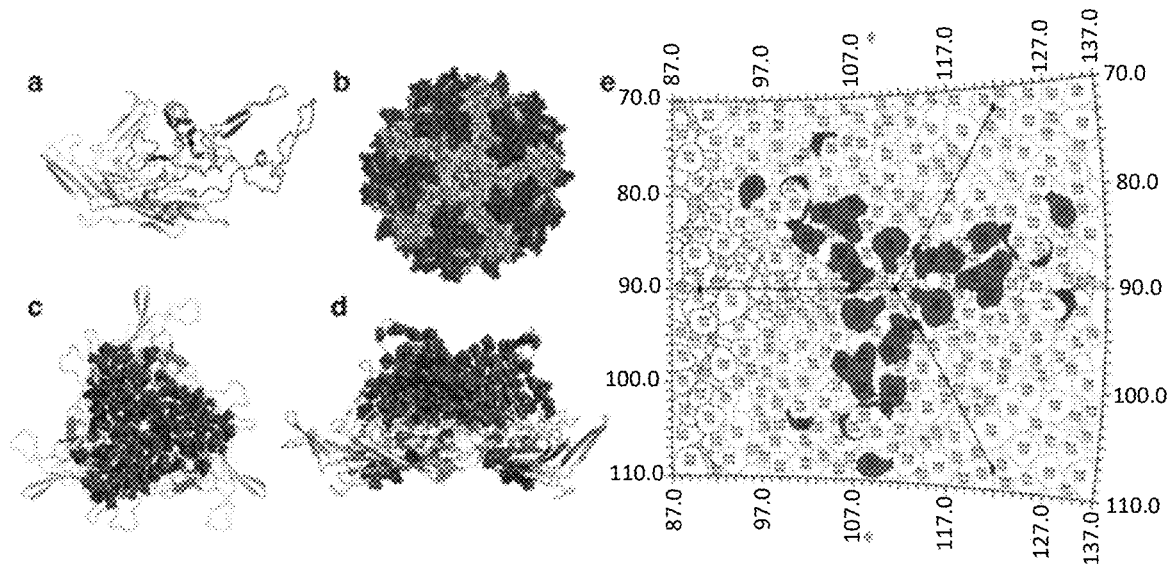
FIG. 2
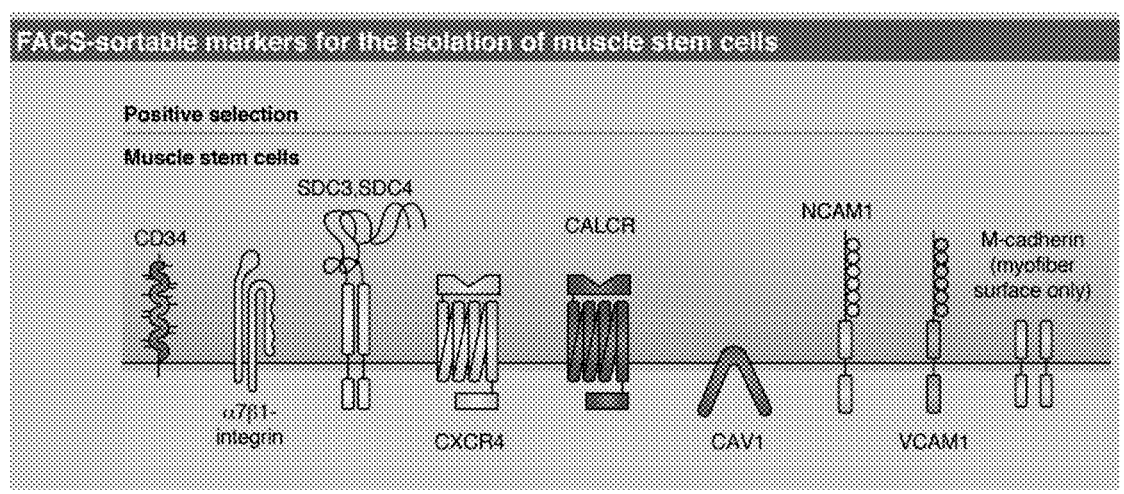

SEQUENCE LISTING

<160> NUMBER OF SEQ ID NOS: 5

<210> SEQ ID NO 1
<211> LENGTH: 1661
<212> TYPE: DNA
<213> ORGANISM: Homo sapiens

<400> SEQUENCE: 1

```
gaaactcgtg agagcccttt ctccagggac agttgctgaa gcttcatcct ttgctctcat      60
tctgtaagtc atagaaaagt ttgaaacatt ctgtctgtgg tagagctcgg gccagctgta     120
gttcattcgc cagtgtgctt ttcttaatat ctaagatggt gcgtgagcag tacactacag     180
ccacagaagg catctgcata gagaggccag agaatcagta tgtctacaaa attggcattt     240
atggctggag aaagcgctgt ctctacttgt ttgttcttct tttactcatc atcctcgttg     300
```

```
tgaatttagc tcttacaatt tggattctta aagtgatgtg gttttctcca gcaggaatgg      360
gccacttgtg tgtaacaaaa gatggactgc gcttggaagg ggaatcagaa tttttattcc      420
cattgtatgc caaagaaata cactccagag tggactcatc tctgcttcta caatcaaccc      480
agaatgtgac tgtaaatgcg cgcaactcag aaggggaggt cacaggcagg ttaaaagtcg      540
gtcccaaaat ggtagaagtc cagaatcaac agtttcagat caactccaac gacggcaagc      600
cactatttac tgtagatgag aaggaagttg tggttggtac agataaactt cgagtaactg      660
ggcctgaagg ggctcttttt gaacattcag tggagacacc ccttgtcaga gccgacccgt      720
ttcaagacct tagattagaa tcccccactc ggagtctaag catggatgcc caaggggtg       780 tgcatattca agctcacgct gggaaaattg aggcgctttc tcaaatggat attcttttc       840 atagtagtga tggaatgctt gtgcttgatg ctgaaactgt gtgcttaccc aagctggtgc      900
aggggacgtg gggtccctct ggcagctcac agagcctcta cgaaatctgt gtgtgtccag      960
atgggaagct gtacctgtct gtggccggtg tgagcaccac gtgccaggag cacagccaca     1020
tctgcctctg agctgcctgc gtcctctcgg tgagctgtgc agtgccggcc ccagatcctc     1080
acacccaggg agcagctgca catcgtgaaa gactgaggca gcgtggatgg gaagtaaacg     1140
cttccagagg aactcagaaa aaattatgtg ccagtgaaag tgtttggaca aaaactacat     1200
gatctcaaaa tgcacgtgga tgtgagacac aaaagttgac aaaatggaaa agcaatgtgt     1260
ttttccactg gattaatttt caccggaaca attgcgaatt ctctctgcct cgcctccccc     1320
tatcttgtcc gtgtgggcac acactgagtg ttgagttgcc gtgtggagtt aatgtatgac     1380
gctccactgt ggatatctaa tgccctgttg agagtagcct tgctcagtac taaaatgccc     1440
caaagttcta tacagcattt cctttatagc attcaaacct cacatcctcc cttcagttta     1500
atgcaagtaa gtcaggtttc acaagaaaat tttcaagttt tgaagggaat ttgaggttga     1560
tctggttttc aagatgtagt taaaggaata aatcactcaa aattaaactt tctgtatata     1620
gtcaataagc aataaaaacc tcattttttca gagttaaaaa a                        1661
```

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Ile Gly Ser Arg
1               5

<210> SEQ ID NO 3
<211> LENGTH: 2217
<212> TYPE: DNA
<213> ORGANISM: Adeno-associated virus

<400> SEQUENCE: 3

```
atggctgccg atggttatct tccagattgg ctcgaggaca acctctctga gggcattcgc      60
gagtggtggg acctgaaacc tggagccccg aaacccaaag ccaaccagca aaagcaggac     120
aacggccggg gtctggtgct tcctggctac aagtacctcg gacccttcaa cggactcgac     180
aagggggagc ccgtcaacgc ggcggacgca gcggcccctcg agcacgacaa ggcctacgac     240
cagcagctcc aagcgggtga caatccgtac ctgcggtata tcacgccga cgccgagttt     300
```

| | |
|---|---|
| caggagcgtc tgcaagaaga tacgtctttt gggggcaacc tcgggcgcgc agtcttccag | 360 |
| gccaaaaagc gggttctcga acctctgggc ctggttgaat cgccggttaa gacggctcct | 420 |
| ggaaagaaga gaccggtaga gccatcaccc cagcgctctc cagactcctc tacgggcatc | 480 |
| ggcaagaaag gccagcagcc cgcaaaaaag agactcaatt ttgggcagac tggcgactca | 540 |
| gagtcagtcc ccgaccctca accaatcgga gaaccaccag caggcccctc tggtctggga | 600 |
| tctggtacaa tggctgcagg cggtggcgct ccaatggcag acaataacga aggcgccgac | 660 |
| ggagtgggta gttcctcagg aaattggcat gcgattcca catggctggg cgacagagtc | 720 |
| atcaccacca gcacccgcac ctgggccctg cccacctaca caaccaccct ctacaagcaa | 780 |
| atctccaacg ggacctcggg aggaagcacc aacgacaaca cctacttcgg ctacagcacc | 840 |
| ccctgggggt attttgactt caacagattc cactgccact tttcaccacg tgactggcag | 900 |
| cgactcatca acaacaactg gggattccgg cccaagaggc tcaacttcaa gctcttcaac | 960 |
| atccaagtca aggaggtcac gcagaatgaa ggcaccaaga ccatcgccaa taaccttacc | 1020 |
| agcacgattc aggtctttac ggactcggaa taccagctcc cgtacgtgct cggctcggcg | 1080 |
| caccagggct gcctgcctcc gttcccggcg gacgtcttca tgattcctca gtacgggtac | 1140 |
| ctgactctga acaatggcag tcaggctgtg ggccggtcgt ccttctactg cctggagtac | 1200 |
| tttccttctc aaatgctgag aacgggcaac aactttgaat tcagctacaa cttcgaggac | 1260 |
| gtgcccttcc acagcagcta cgcgcacagc cagagcctgg accggctgat gaaccctctc | 1320 |
| atcgaccagt acttgtacta cctgtcccgg actcaaagca cgggcggtac tgcaggaact | 1380 |
| cagcagttgc tattttctca ggccgggcct aacaacatgt cggctcaggc caagaactgg | 1440 |
| ctacccggtc cctgctaccg gcagcaacgc gtctccacga cactgtcgca gaacaacaac | 1500 |
| agcaactttg cctggacggg tgccaccaag tatcatctga atggcagaga ctctctggtg | 1560 |
| aatcctggcg ttgccatggc tacccacaag gacgacgaag agcgattttt tccatccagc | 1620 |
| ggagtcttaa tgtttgggaa acagggagct ggaaaagaca cgtggacta tagcagcgtg | 1680 |
| atgctaacca gcgaggaaga aataaagacc accaacccag tggccacaga acagtacggc | 1740 |
| gtggtggccg ataacctgca acagcaaaac gccgctccta ttgtagggc cgtcaatagt | 1800 |
| caaggagcct tacctggcat ggtgtggcag aaccgggacg tgtacctgca gggtcccatc | 1860 |
| tgggccaaga ttcctcatac ggacggcaac tttcatccct cgccgctgat gggaggcttt | 1920 |
| ggactgaagc atccgcctcc tcagatcctg attaaaaaca cacctgttcc cgcggatcct | 1980 |
| ccgaccacct tcaatcaggc caagctggct tctttcatca cgcagtacag taccggccag | 2040 |
| gtcagcgtgg agatcgagtg ggagctgcag aaggagaaca gcaaacgctg gaacccagag | 2100 |
| attcagtaca cttccaacta ctacaaatct acaaatgtgg actttgctgt caatactgag | 2160 |
| ggtacttatt ccgagcctcg ccccattggc acccgttacc tcacccgtaa tctgtaa | 2217 |

<210> SEQ ID NO 4
<211> LENGTH: 738
<212> TYPE: PRT
<213> ORGANISM: Adeno-associated virus

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro

```
            35                  40                  45
Gly Tyr Lys Tyr Leu Gly Pro Phe Asn Gly Leu Asp Lys Gly Glu Pro
 50                  55                  60
Val Asn Ala Ala Asp Ala Ala Leu Glu His Asp Lys Ala Tyr Asp
 65                  70                  75                  80
Gln Gln Leu Gln Ala Gly Asp Asn Pro Tyr Leu Arg Tyr Asn His Ala
                 85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
                115                 120                 125
Leu Gly Leu Val Glu Ser Pro Val Lys Thr Ala Pro Gly Lys Lys Arg
                130                 135                 140
Pro Val Glu Pro Ser Pro Gln Arg Ser Pro Asp Ser Thr Gly Ile
145                 150                 155                 160
Gly Lys Lys Gly Gln Gln Pro Ala Lys Lys Arg Leu Asn Phe Gly Gln
                165                 170                 175
Thr Gly Asp Ser Glu Ser Val Pro Asp Pro Gln Pro Ile Gly Glu Pro
                180                 185                 190
Pro Ala Gly Pro Ser Gly Leu Gly Ser Gly Thr Met Ala Ala Gly Gly
                195                 200                 205
Gly Ala Pro Met Ala Asp Asn Asn Glu Gly Ala Asp Gly Val Gly Ser
                210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
                260                 265                 270
Asn Thr Tyr Phe Gly Tyr Ser Thr Pro Trp Gly Tyr Phe Asp Phe Asn
                275                 280                 285
Arg Phe His Cys His Phe Ser Pro Arg Asp Trp Gln Arg Leu Ile Asn
                290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Leu Pro Pro Phe
                355                 360                 365
Pro Ala Asp Val Phe Met Ile Pro Gln Tyr Gly Tyr Leu Thr Leu Asn
                370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Asn Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
                435                 440                 445
Ser Arg Thr Gln Ser Thr Gly Gly Thr Ala Gly Thr Gln Gln Leu Leu
                450                 455                 460
```

```
Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
                580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 5
<211> LENGTH: 738
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

-continued

```
Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
           100                 105                 110

Asn Leu Gly Arg Ala Val Phe Gln Ala Lys Lys Arg Val Leu Glu Pro
       115                 120                 125

Leu Gly Leu Val Glu Ser Pro Val Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
               165                 170                 175

Thr Gly Asp Ser Glu Ser Val Pro Asp Pro Gln Pro Ile Gly Glu Pro
           180                 185                 190

Pro Ala Gly Pro Ser Gly Leu Gly Ser Gly Thr Met Ala Ala Gly Gly
       195                 200                 205

Gly Ala Pro Met Ala Asp Asn Asn Glu Gly Ala Asp Gly Val Gly Ser
   210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
               245                 250                 255

Leu Tyr Lys Gln Ile Ser Asn Gly Thr Ser Gly Gly Ser Thr Asn Asp
           260                 265                 270

Asn Thr Tyr Phe Gly Tyr Ser Thr Pro Trp Gly Tyr Phe Asp Phe Asn
       275                 280                 285

Arg Phe His Cys His Phe Ser Pro Arg Asp Trp Gln Arg Leu Ile Asn
   290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
               325                 330                 335

Asn Asn Leu Thr Ser Thr Ile Gln Val Phe Thr Asp Ser Glu Tyr Gln
           340                 345                 350

Leu Pro Tyr Val Leu Gly Ser Ala His Gln Gly Cys Leu Pro Pro Phe
       355                 360                 365

Pro Ala Asp Val Phe Met Ile Pro Gln Tyr Gly Tyr Leu Thr Leu Asn
   370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
               405                 410                 415

Asn Phe Glu Asp Val Pro Phe His Ser Ser Tyr Ala His Ser Gln Ser
           420                 425                 430

Leu Asp Arg Leu Met Asn Pro Leu Ile Asp Gln Tyr Leu Tyr Tyr Leu
       435                 440                 445

Ser Arg Thr Gln Ser Thr Gly Gly Thr Ala Gly Thr Gln Gln Leu Leu
   450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
               485                 490                 495
```

-continued

```
Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Tyr Ile
            580                 585                 590

Gly Ser Arg Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu
```

INCREASING TISSUE SPECIFIC GENE DELIVERY BY CAPSID MODIFICATION

CROSS-REFERENCE TO RELATED APPLICATIONS

This application is a national stage application under 35 U.S.C. § 371 of PCT Application No. PCT/US2019/022353, filed Mar. 14, 2019, which claims priority under 35 U.S.C. § 119 (e) to U.S. Provisional Application Ser. No. 62/644,317, filed Mar. 16, 2018, the contents of which are incorporated by reference herein.

STATEMENT REGARDING GOVERNMENT SUPPORT

This invention was made with government support under grant no. TR001068 from the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 26, 2019, is named 106887-7170_SL.txt and is 18,492 bytes in size.

BACKGROUND

Efforts have been made to modify AAV capsids for improved gene delivery. For example, WO 2017/165859A1 describes a viral capsid modification where Cas9 is fused or conjugated to viral capsid protein to promote customizable gene editing. Further references have describe using DNA family shuffling (Grimm and Kay), lysine substitutions to AAVrh74 (US 2015/006556), mutations at positions 195, 199, 201, or 202 of AAVrh74 (U.S. Pat. No. 9,840,719), and modifications to AAVrh48 (EP 2359866). Still further references detail random peptide libraries being displayed on an AAV surface (e.g., Muller (2003) Nat. Biotechnol., Perabo (2003) Mol. Ther., and U.S. Pat. No. 7,588,722 (Grimm and Kay)).

Gene therapy treatments for Muscular Dystrophies will require systemic delivery of genes to muscle cells throughout the body. The most efficient delivery option is to use the body's circulatory system to distribute the virus to the peripheral muscle cells. An issue for systemic delivery is that most serotypes of AAV have a natural propensity to infect liver cells [1]. There are approximately 20 times more liver cells than muscle cells in the body, which the virus must traverse during systemic delivery [2]. It is estimated that more than 50% of AAV vectors remain trapped in the liver after a systemic intravenous injection.

Currently more than 50% of systemically injected virus is lost in the liver where little therapeutic effect is usually realized [4]. By de-targeting vector delivery to the liver and increasing muscle specific binding and transduction may significantly improve muscle specific gene expression and therapeutic benefit to the patient while reducing potential side effects. Currently clinical trials for the treatment of Duchene Muscular Dystrophy require the delivery of high levels of vector (>5E+12 vector genomes per kilogram) to try to achieve therapeutic levels of gene expression in the muscle. Muscle-specific promoters are used to reduce "off target" gene expression but do nothing towards increasing overall levels of gene expression. By increasing the efficiency of muscle-specific transduction, the overall dose required to achieve a therapeutic benefit may be significantly reduced.

The present disclosure addresses the limitations of the prior art and provides related advantages as well.

SUMMARY

Applicant proposes an approach to increase the systemic delivery of vector to muscle cells would be to reduce or eliminate the infection of liver cells as the virus circulates. Applicant hypothesizes that modified AAVrh74 capsids target muscle myoblasts and satellite cells more efficiently than unmodified AAVrh74 vectors.

The present disclosure relates to modified viral capsid protein that comprises, or alternatively consists essentially of, or yet further consists of, a viral capsid protein modified by amino acid substitution or insertion of between 1 to 7 amino acid. Applicant has generated three mutants. One of the mutants (AAVmut4, asparagine to isoleucine at amino acid 502 of VP1 capsid) Increases gene delivery globally to all tissues tested up to 56-fold (between 3 and 56-fold Increase depending on tissue) higher transduction efficiency. Another mutant (AAVmut5, tryptophan to arginine at amino acid 505 of VP1 capsid) increases gene delivery to the heart almost 50-fold over AAVrh74. A third mutant (AAVYIG or AAVYIGSR591) targets a receptor found primarily on satellite cells which are considered muscle stem cells although the satellite cell tropism has yet to be confirmed by IHC staining. Notably, based on Applicant's knowledge of AAV crystal structures and alpha 7 beta 1 integrin to design AAVYIG or AAVYIGSR 591 is believed to have a higher affinity for skeletal muscle and lower affinity for liver.

Not to be bound by theory, Applicant provides methods to achieve therapeutic benefits to a patient by increasing the effective dose that reaches the target tissue such as the heart or muscle without increasing overall dose to the patient. By reducing the overall dose required to achieve a therapeutic benefit, fewer viral antigens are delivered to the patient, ideally resulting in reduced immune responses to the vector and increased safety. Manufacturing enough gene therapy drug product to conduct late stage clinical trials is a major hurdle in further development. Reducing the dose requirements to achieve therapeutic benefit will result in reduced manufacturing requirements, reduced costs of manufacturing, faster clinical trial development and greater ability to treat more patients.

Accordingly, this disclosure relates to modified capsid proteins, isolated polynucleotides, methods for the preparation of modified capsid proteins, recombinant viral particles and recombinant expression systems for the generation of modified viral particles. One aspect of the disclosure relates to a modified viral capsid protein that comprises, or alternatively consists essentially of, or yet further consists of, a viral capsid protein modified by amino acid substitution or insertion of between 1 to 7 amino acid. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In some embodiments, the modification comprises the substitution of tryptophan to arginine at amino acid 505 of the VP1 of AAVrh74. In some embodiments, the modification targets a receptor found primarily on satellite cells, optionally muscle stem cells. In some embodiments, the modification is an insertion of the peptide YIG or YIGSR (Tyr-Ile-Gly-Ser-Arg) (SEQ ID NO: 2) at amino acid position 591 of the VP1 of AAVrh74 or an equivalent thereof. In some embodiments, this peptide has a has a high affinity for Alpha 7 beta 1 integrin and/or is positioned in a region that is likely to alter normal rh74 receptor binding.

Also disclosed herein is an isolated polynucleotide encoding a modified viral capsid protein that comprises, or alternatively consists essentially of, or yet further consists of, a modified viral capsid protein modified by amino acid substitution or insertion of between 1 to 7 amino acid. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In some embodiments, the modification comprises the substitution of tryptophan to arginine at amino acid 505 of the VP1 of AAVrh74. In some embodiments, the modification targets a receptor found primarily on satellite cells, optionally muscle stem cells. In some embodiments, the modification is an insertion of the peptide YIG or YIGSR (SEQ ID NO: 2) at amino acid position 591 of the VP1 of AAVrh74 or an equivalent thereof. In some embodiments, this peptide has a has a high affinity for Alpha 7 beta 1 integrin and/or is positioned in a region that is likely to alter normal rh74 receptor binding.

Disclosed herein is a recombinant viral particle that comprises or alternatively consists essentially of, or yet further consists of, a modified capsid protein that comprises, or alternatively consists essentially of, or yet further consists of, a modified viral capsid protein modified by amino acid substitution or insertion of between 1 to 7 amino acid. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In some embodiments, the modification comprises the substitution of tryptophan to arginine at amino acid 505 of the VP1 of AAVrh74. In some embodiments, the modification targets a receptor found primarily on satellite cells, optionally muscle stem cells. In some embodiments, the modification is an insertion of the peptide YIG or YIGSR (SEQ ID NO: 2) at amino acid position 591 of the VP1 of AAVrh74. In some embodiments, this peptide has a high affinity for Alpha 7 beta 1 integrin and/or is positioned in a region that is likely to alter normal rh74 receptor binding. In particular aspects, the recombinant viral particle comprises or alternatively consists essentially of 5 or more modified capsid proteins per viral particle (and/or per modified viral capsid).

In other aspects, the recombinant viral particle comprises or alternatively consists essentially of between 1 and 5 modified capsid proteins per viral particle (and/or per modified viral capsid). Further aspects contemplate a polynucleotide encoding the viral capsid protein modified by amino acid substitution or insertion of between 1 to 7 amino acid disclosed herein. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In some embodiments, the modification comprises the substitution of tryptophan to arginine at amino acid 505 of the VP1 of AAVrh74. In some embodiments, the modification targets a receptor found primarily on satellite cells, optionally muscle stem cells. In some embodiments, the modification is an insertion of the peptide YIG or YIGSR (SEQ ID NO: 2) at amino acid position 591 of the VP1 of AAVrh74. In some embodiments, this peptide has a has a high affinity for Alpha 7 beta 1 integrin and/or is positioned in a region that is likely to alter normal rh74 receptor binding.

Also provided are the modified capsids as disclosed herein that optionally comprise a transgene or CRISPR system for gene modification. Further provided are polynucleotides encoding the modified capsids and vectors encoding said polynucleotides, as well as the complements and equivalents of each thereof. Still further aspects relate to a host cell producing the viral particle and/or comprising the vector disclosed herein. Still further aspects relate to an expression system for the production of the viral particle disclosed herein.

This disclosure also provides compositions comprising a carrier and one or more of a modified capsids, a polynucleotide, a vector, a plasmid, a host cell, or expression system. Further provided is a kit comprising one or more of a modified capsid protein, a polynucleotide, vector, plasmid, host cell, or expression system and instructions for use.

Further disclosed herein is a method of treating a target diseases or dysfunctional tissue in a subject in need thereof, comprising, or alternatively consisting essentially of, or yet further consisting of, administering to the subject an effective amount of a recombinant viral particle that comprises, or alternatively consists essentially of, or yet further consists of, a modified capsid protein that comprises, or alternatively consists essentially of, or yet further consists of, a viral capsid protein modified by amino acid substitution or insertion of between 1 to 7 amino acid. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In further embodiments, this viral particle increases the efficacy of treatment delivery between about 3 and 56 fold for the diseased or dysfunctional tissue relative to AAVrh74. In some embodiments, the modification comprises the substitution of tryptophan to arginine at amino acid 505 of the VP1 of AAVrh74. In further embodiments, the diseases or dysfunctional tissue is heart tissue. **In still further embodiments, this viral particle increases the efficacy of treatment delivery between about 50 fold or more to heart tissue relative to AAVrh74. In some embodiments, the modification targets a receptor found primarily on satellite cells, optionally muscle stem cells. In some embodiments, the modification is an insertion of the peptide YIG or YIGSR (SEQ ID NO: 2) at amino acid position 591 of the VP1 of AAVrh74. In some embodiments, this peptide has a has a high affinity for Alpha 7 beta 1 integrin and/or is positioned in a region that is likely to alter normal rh74 receptor binding. In some embodiments, the viral particle comprises an effective amount of a treatment suitable for the disease or dysfunctional tissue. In some embodiments, the treatment is CRISPR/Cas9 based gene editing.

BRIEF DESCRIPTION OF THE FIGURES

FIG. 1 shows structural analysis of the adeno-associated virus serotype 9 (AAV9) capsid library. (a) Cartoon representation of the AAV9 VP3 subunit monomer obtained using SWISS-MODEL with crystal structure of AAV8 serving as template (pdb id: 2QA0). The GH loop containing amino acids 390-627 (VP1 numbering) is colored in grey. (b) Surface rendering of an AAV9 capsid model with 60 VP3 subunits generated using T=1 icosahedral symmetry coordinates on VIPERdb. GH loop regions from different VP3 subunits, surrounding the icosahedral fivefold pore and interdigitating at the threefold symmetry axis are highlighted in grey. (c) Cartoon of AAV9 VP3 subunit trimer generated on VIPERdb with point mutations of 43 representative clones from the AAV9 library depicted by grey spheres. (d) Side view of capsid trimer (90° rotation) showing a majority of point mutations (grey spheres) clustered on the outer loops. (e) Spherical roadmap projection of surface residues within the capsid trimer region. Residues highlighted in gray represent a subset of ten AAV9 variants containing altered residues prominently located on the capsid surface. Figure reproduced from Pulicherla et al [7].

FIG. 2 shows FACS sortable markers for the isolation of muscle stem cells. Figure reproduced from Wang et. al., [13].

DETAILED DESCRIPTION

Figure 3:
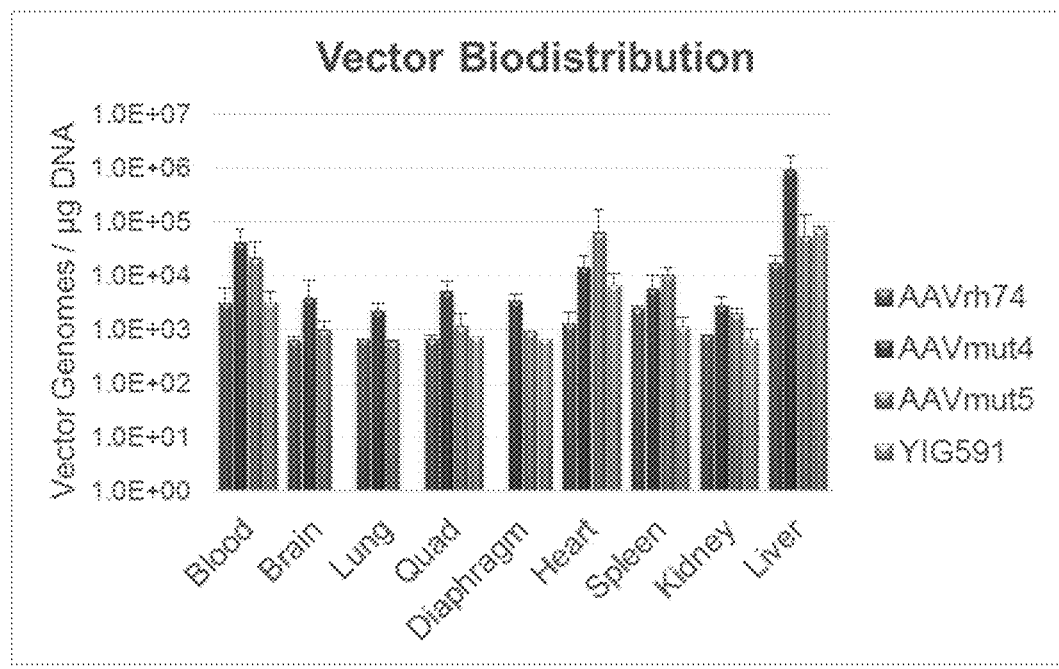
FIG. 3 shows AAVrh74 mutant vector biodistribution. CD-1 male mice were injected intravenously with 1E+11 Vg of AAVrh74 or two mutants of AAVrh74 capsid/lucEYFP reporter virus and 3 weeks later tissues were harvested and assayed for vector genome copies by qPCR.

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

The practice of the present technology will employ, unless otherwise indicated, conventional techniques of tissue culture, immunology, molecular biology, microbiology, cell biology, and recombinant DNA, which are within the skill of the art.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

Throughout this disclosure, various publications, patents and published patent specifications are referenced by an identifying citation or by an Arabic numeral. The full citation for the publications identified by an Arabic numeral are found immediately preceding the claims. The disclosures of these publications, patents and published patent specifications are hereby incorporated by reference into the present disclosure in their entirety to more fully describe the state of the art to which this invention pertains.

Definitions

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, $2^{nd}$ edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (R. I. Freshney, ed. (1987)).

As used in the description of the invention and the appended claims, the singular forms "a," "an" and "the" are intended to include the plural forms as well, unless the context clearly indicates otherwise.

As used herein, the term "comprising" is intended to mean that the compositions and methods include the recited elements, but do not exclude others. As used herein, the transitional phrase consisting essentially of (and grammatical variants) is to be interpreted as encompassing the recited materials or steps and those that do not materially affect the basic and novel characteristic(s) of the recited embodiment. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

Also as used herein, "and/or" refers to and encompasses any and all possible combinations of one or more of the associated listed items, as well as the lack of combinations when interpreted in the alternative ("or").

The term "cell" as used herein may refer to either a prokaryotic or eukaryotic cell, optionally obtained from a subject or a commercially available source.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human, e.g., HEK293 cells and 293T cells.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

The terms "equivalent" or "biological equivalent" are used interchangeably when referring to a particular molecule, biological, or cellular material and intend those having minimal homology while still maintaining desired structure or functionality. Non-limiting examples of equivalent polypeptides, include a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, or a polypeptide which is encoded by a polynucleotide or its complement that hybridizes under conditions of high stringency to a polynucleotide encoding such polypeptide sequences. Conditions of high stringency are described herein and incorporated herein by reference. Alternatively, an equivalent thereof is a polypeptide encoded by a polynucleotide or a complement thereto, having at least 70%, or alternatively at least 75%, or alternatively 80%, or alternatively at least 85%, or alternatively at least 90%, or alternatively at least 95% identity, or at least 97% sequence identity to the reference polynucleotide, e.g., the wild-type polynucleotide.

Non-limiting examples of equivalent polypeptides, include a polynucleotide having at least 60%, or alternatively at least 65%, or alternatively at least 70%, or alternatively at least 75%, or alternatively 80%, or alternatively at least 85%, or alternatively at least 90%, or alternatively at least 95%, or alternatively at least 97%, identity to a reference polynucleotide. An equivalent also intends a polynucleotide or its complement that hybridizes under conditions of high stringency to a reference polynucleotide.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity can be determined by incorporating them into clustalW (available at the web address:genome.jp/tools/clustalw/, last accessed on Jan. 13, 2017).

"Homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "isolated" as used herein refers to molecules or biologicals or cellular materials being substantially free from other materials.

As used herein, the term "functional" may be used to modify any molecule, biological, or cellular material to intend that it accomplishes a particular, specified effect.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, the term "recombinant expression system" refers to a genetic construct or constructs for the expression of certain genetic material formed by recombination.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of vectors are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro.

Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene. Further details as to modern methods of vectors for use in gene transfer may be found in, for example, Kotterman et al. (2015) Viral Vectors for Gene Therapy: Translational and Clinical Outlook Annual Review of Biomedical Engineering 17.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. Ads do not require integration into the host cell genome. Recombinant Ad derived vectors, particularly those that reduce the potential for recombination and generation of wild-type virus, have also been constructed. Such vectors are commercially available from sources such as Takara Bio USA (Mountain View, CA), Vector Biolabs (Philadelphia, PA), and Creative Biogene (Shirley, NY). Wild-type AAV has high infectivity and specificity integrating into the host cell's genome. See, Wold and Toth (2013) Curr. Gene. Ther. 13(6):421-433, Hermonat & Muzyczka (1984) Proc. Natl. Acad. Sci. USA 81:6466-6470, and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

As used herein, the term "viral capsid" or "capsid" refers to the proteinaceous shell or coat of a viral particle. Capsids function to encapsidate, protect, transport, and release into host cell a viral genome. Capsids are generally comprised of oligomeric structural subunits of protein ("capsid proteins"). As used herein, the term "encapsidated" means enclosed within a viral capsid.

As used herein, the term "helper" in reference to a virus or plasmid refers to a virus or plasmid used to provide the additional components necessary for replication and packaging of a viral particle or recombinant viral particle, such as the modified AAV disclosed herein. The components encoded by a helper virus may include any genes required for virion assembly, encapsidation, genome replication, and/or packaging. For example, the helper virus may encode necessary enzymes for the replication of the viral genome. Non-limiting examples of helper viruses and plasmids suitable for use with AAV constructs include pHELP (plasmid), adenovirus (virus), or herpesvirus (virus).

As used herein, the term "AAV" is a standard abbreviation for adeno-associated virus. Adeno-associated virus is a single-stranded DNA parvovirus that grows only in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized after the publication dates of the reviews because it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3: 1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector." Thus, production of AAV vector particle necessarily includes production of AAV vector, as such a vector is contained within an AAV vector particle.

Adeno-associated virus (AAV) is a replication-deficient parvovirus, the single-stranded DNA genome of which is about 4.7 kb in length including two 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928, incorporated herein by reference. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and pi 9), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible.

Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics. Recombinant AAV (rAAV) genomes of the invention comprise a nucleic acid molecule encoding γ-sarcoglycan (e.g., SEQ ID NO: 1) and one or more AAV ITRs flanking the nucleic acid molecule. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). The nucleotide sequences of the genomes of various AAV serotypes are known in the art.

The term "Cas9" refers to a CRISPR associated endonuclease referred to by this name. Non-limiting exemplary Cas9s are provided herein, e.g. the Cas9 provided for in UniProtKB G3ECR1 (CAS9_STRTR) or the *Staphylococcus aureus* Cas9, as well as the nuclease dead Cas9, orthologs and biological equivalents each thereof. Orthologs include but are not limited to *Streptococcus pyogenes* Cas9 ("spCas9"); Cas 9 from *Streptococcus thermophiles, Legionella pneumophilia, Neisseria lactamica, Neisseria meningitides, Francisella novicida*; and Cpf1 (which performs cutting functions analogous to Cas9) from various bacterial species including *Acidaminococcus* spp. and *Francisella novicida* U112.

As used herein, the term "CRISPR" refers to a technique of sequence specific genetic manipulation relying on the clustered regularly interspaced short palindromic repeats pathway. CRISPR can be used to perform gene editing and/or gene regulation, as well as to simply target proteins to a specific genomic location. Gene editing refers to a type of genetic engineering in which the nucleotide sequence of a target polynucleotide is changed through introduction of deletions, insertions, or base substitutions to the polynucleotide sequence. In some aspects, CRISPR-mediated gene editing utilizes the pathways of non-homologous end-joining (NHEJ) or homologous recombination to perform the edits. Gene regulation refers to increasing or decreasing the production of specific gene products such as protein or RNA.

The term "gRNA" or "guide RNA" as used herein refers to the guide RNA sequences used to target specific genes for correction employing the CRISPR technique. Techniques of designing gRNAs and donor therapeutic polynucleotides for target specificity are well known in the art. For example, Doench, J., et al. Nature biotechnology 2014; 32(12):1262-7, Mohr, S. et al. (2016) FEBS Journal 283: 3232-38, and Graham, D., et al. Genome Biol. 2015; 16: 260. gRNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and trans-activating CRIPSPR RNA (tracrRNA). In some aspects, a gRNA is synthetic (Kelley, M. et al. (2016) J of Biotechnology 233 (2016) 74-83). As used herein, a biological equivalent of a gRNA includes but is not limited to polynucleotides or targeting molecules that can guide a Cas9 or equivalent thereof to a specific nucleotide sequence such as a specific region of a cell's genome.

A "composition" is intended to mean a combination of active polypeptide, polynucleotide or antibody and another compound or composition, inert (e.g., a detectable label) or active (e.g., a gene delivery vehicle).

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject" of diagnosis or treatment is a cell or an animal such as a mammal, or a human. A subject is not limited to a specific species and includes non-human animals subject to diagnosis or treatment and are those subject to infections or animal models, for example, simians, murines, such as, rats, mice, chinchilla, canine, such as dogs, leporids, such as rabbits, livestock, sport animals, and pets. Human patients are included within the term as well.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected) or a group of tissues making up an organ or part or region of the body of an organism. The tissue may comprise a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

MODES OF CARRYING OUT THE DISCLOSURE

Modified Viral Capsids and Methods of Preparation

AAV vector delivery currently relies on the use of serotype selection for tissue targeting based on the natural tropism of the virus or by the direct injection into target tissues. If systemic delivery is required to achieve maximal therapeutic benefit, then serotype selection is the only available option for tissue targeting combined with tissue specific promoters. As described herein, Applicant has approach identified specific amino acids responsible for receptor binding and entry thereby reducing the need for elaborate mutagenesis studies to identify critical amino acids in AAVrh74 [7-11] (FIG. 1). With the critical regions for liver de-targeting identified, Applicant has developed modified capsids that enrich for muscle specific vector transduction. The positive impact of combining reduced vector loss in the liver with muscle cell specific delivery of the gene of interest will greatly improve the chances of meeting the threshold for clinical efficacy in the systemic treatment of neuromuscular diseases.

This disclosure relates to modified capsid proteins, isolated polynucleotides, methods for the preparation of modified capsid proteins, recombinant viral particles and recombinant expression systems for the generation of modified viral particles. One aspect of the disclosure relates to a modified viral capsid protein that comprises, or alternatively consists essentially of, or yet further consists of, a viral capsid protein modified by amino acid substitution or insertion of between 1 to 7 amino acid. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In some embodiments, the modification comprises the substitution of tryptophan to arginine at amino acid 505 of the VP1 of AAVrh74. In some embodiments, the modification targets a receptor found primarily on satellite cells, optionally muscle stem cells. In some embodiments, the modification is an insertion of the peptide YIG or YIGSR (Tyr-Ile-Gly-Ser-Arg) (SEQ ID NO: 2) at amino acid position 591 of the VP1 of AAVrh74. In some embodiments, this peptide has a has a high affinity for Alpha 7 beta 1 integrin and/or is positioned in a region that is likely to alter normal rh74 receptor binding. The modified capsids can be incorporated into other viral delivery systems.

In a further aspect, the modified viral particles further comprise a transgene for gene modification and/or a CRISPR system for gene modification.

Also disclosed herein is an isolated polynucleotide encoding a modified viral capsid protein that comprises, or alternatively consists essentially of, or yet further consists of, a modified viral capsid protein modified by amino acid substitution or insertion of between 1 to 7 amino acid. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In some aspect, other amino acids in the peptide are modified but this substitution is maintained. In some embodiments, the modification comprises the substitution of tryptophan to arginine at amino acid 505 of the VP1 of AAVrh74. In some aspect, other amino acids in the peptide are modified but this substitution is maintained. In some embodiments, the modification targets a receptor found primarily on satellite cells, optionally muscle stem cells. In some embodiments, the modification is an insertion of the peptide YIG or YIGSR (SEQ ID NO: 2) at amino acid position 591 of the VP1 of AAVrh74. In some aspect, other amino acids in the peptide are modified but this substitution is maintained. In some embodiments, this peptide has a has a high affinity for Alpha 7 beta 1 integrin and/or is positioned in a region that is likely to alter normal rh74 receptor binding.

Disclosed herein is a recombinant viral particle that comprises or alternatively consists essentially of, or yet further consists of, a modified capsid protein that comprises, or alternatively consists essentially of, or yet further consists of, a modified viral capsid protein modified by amino acid substitution or insertion of between 1 to 7 amino acid. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In some aspect, other amino acids in the peptide are modified but this substitution is maintained. In further embodiments, this viral particle increases the efficacy of treatment delivery between about 3 and 56 fold for the diseased or dysfunctional tissue relative to AAVrh74. In some embodiments, the modification comprises the substitution of tryptophan to arginine at amino acid 505 of the VP1 of AAVrh74. In some aspect, other amino acids in the peptide are modified but this substitution is maintained. In further embodiments, the diseases or dysfunctional tissue is heart tissue. In still further embodiments, this viral particle increases the efficacy of treatment delivery between about 50 fold or more to heart tissue relative to AAVrh74. In some embodiments, the modification targets a receptor found primarily on satellite cells, optionally muscle stem cells. In some embodiments, the modification is an insertion of the peptide YIG or YIGSR (SEQ ID NO: 2) at amino acid position 591 of the VP1 of AAVrh74. In some aspect, other amino acids in the peptide are modified but this substitution is maintained. In some embodiments, this peptide has a has a high affinity for Alpha 7 beta 1 integrin and/or is positioned in a region that is likely to alter normal rh74 receptor binding. In some embodiments, the viral particle comprises an effective amount of a treatment suitable for the disease or dysfunctional tissue. In some embodiments, the treatment is CRISPR/Cas9 based gene editing.

The modified virus, e.g., AAV, can be packaged using a viral packaging system such as a retroviral, adenoviral, herpes virus, or baculovirus packaging system. In some embodiments, packaging is achieved by using a helper virus or helper plasmid and a cell line. The helper virus or helper plasmid contains elements and sequences that facilitate the delivery of genetic materials into cells. In another aspect, the helper plasmid or a polynucleotide comprising the helper plasmid is stably incorporated into the genome of a packaging cell line, such that the packaging cell line does not require additional transfection with a helper plasmid.

A helper plasmid may comprise, for example, at least one viral helper DNA sequence derived from a replication-incompetent viral genome encoding in trans all virion proteins required to package a replication incompetent AAV, and for producing virion proteins capable of packaging the replication-incompetent AAV at high titer, without the production of replication-competent AAV. The viral DNA sequence lacks the region encoding the native enhancer and/or promoter of the viral 5' LTR of the virus, and lacks both the psi function sequence responsible for packaging helper genome and the 3' LTR, but encodes a foreign polyadenylation site, for example the SV40 polyadenylation site, and a foreign enhancer and/or promoter which directs efficient transcription in a cell type where virus production is desired. The virus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter. The helper plasmid may consist of two retroviral helper DNA sequences encoded by plasmid based expression vectors, for example where a first helper sequence contains a cDNA encoding the gag and pol proteins of ecotropic MMLV or GALV and a second helper sequence contains a cDNA encoding the env protein. The Env gene, which determines the host range, may be derived from the genes encoding xenotropic, amphotropic, ecotropic, polytropic (mink focus forming) or 10A1 murine leukemia virus env proteins, or the Gibbon Ape Leukemia Virus (GALV env protein, the Human Immunodeficiency Virus env (gp160) protein, the Vesicular Stomatitus Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell.

In the packaging process, the helper plasmids and the plasmids encoding the AAV viral proteins are transiently co-transfected into a first population of mammalian cells that are capable of producing virus, such as human embryonic kidney cells, for example 293 cells (ATCC No. CRL1573, ATCC, Rockville, Md.) to produce high titer recombinant retrovirus-containing supernatants. In another method of the invention this transiently transfected first population of cells is then co-cultivated with mammalian target cells, for example human lymphocytes, to transduce the target cells with the foreign gene at high efficiencies.

Compositions

Also provided by this invention is a composition or kit comprising any one or more of the viral vectors, isolated cells, packaging system, viral particles as described herein and a carrier. In one aspect, the carrier is a pharmaceutically acceptable carrier. These compositions can be used therapeutically as described herein and can be used in combination with other known therapies.

Methods of Administering Modified Viral Particles

Provided herein is a non-human transgenic animal comprising a modified viral capsid protein modified by amino acid substitution or insertion of between 1 to 7 amino acid. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In some aspect, other amino acids in the peptide are modified but this substitution is maintained. In some embodiments, the modification comprises the substitution of tryptophan to arginine at amino acid 505 of the VP1 of AAVrh74. In some aspect, other amino acids in the peptide are modified but this substitution is maintained. In some embodiments, the modification targets a receptor found primarily on satellite cells, optionally muscle stem cells. In some embodiments, the modification is an insertion of the peptide YIG or YIGSR (SEQ ID NO: 2) at amino acid position 591 of the VP1 of AAVrh74. In some aspect, other amino acids in the peptide are modified but this substitution is maintained. In some embodiments, this peptide has a has a high affinity for Alpha 7 beta 1 integrin and/or is positioned in a region that is likely to alter normal rh74 receptor binding.

Disclosed herein is a method of gene editing comprising, consisting essentially of, or yet further consisting of, contacting a cell with a recombinant viral particle comprising or alternatively consisting essentially of a modified capsid wherein the modified capsid comprises or consists essentially of a modified viral capsid protein comprising or alternatively consisting essentially of, or yet further consisting of modified viral capsid protein modified by amino acid substitution or insertion of between 1 to 7 amino acid. In some embodiments, viral capsid protein is a VP1, optionally of AAVrh74. In some aspect, other amino acids in the peptide are modified but this substitution is maintained. In further embodiments, the modification comprises the substitution of isoleucine for asparagine at amino acid position 502 of the VP1 of AAVrh74 or an equivalent modification. In some aspect, other amino acids in the peptide are modified but this substitution is maintained. In some embodiments, the modification comprises the substitution of tryptophan to arginine at amino acid 505 of the VP1 of AAVrh74. In some aspect, other amino acids in the peptide are modified but this substitution is maintained. In some embodiments, the modification targets a receptor found primarily on satellite cells, optionally muscle stem cells. In some embodiments, the modification is an insertion of the peptide YIG or YIGSR (SEQ ID NO: 2) at amino acid position 591 of the VP1 of AAVrh74. In some aspect, other amino acids in the peptide are modified but this substitution is maintained. In some embodiments, this peptide has a has a high affinity for Alpha 7 beta 1 integrin and/or is positioned in a region that is likely to alter normal rh74 receptor binding. In some embodiments, the contact is in vivo or in vitro. In some embodiments, the viral particle comprises one or more polynucleotides, and at least one of the polynucleotides comprises or consists essentially of, or yet further consists of a polynucleotide encoding a guide RNA (gRNA). In some aspects, at least one of the polynucleotides comprises or alternatively consists essentially of, or yet further consists of a therapeutic polypeptide. In some embodiments, the viral particle comprises a Cas9 or an equivalent thereof.

Further disclosed herein is a method of gene editing in a subject in need thereof, comprising administering to the subject an effective amount recombinant viral particle comprising or alternatively consisting essentially of a modified capsid wherein the modified capsid comprises a modified capsid wherein the modified capsid comprises a modified viral capsid protein comprising or alternatively consisting essentially of, or yet further consisting of modified viral capsid protein modified by amino acid substitution or insertion of between 1 to 7 amino acid. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In some aspect, other amino acids in the peptide are modified but this substitution is maintained. In some embodiments, the modification comprises the substitution of tryptophan to arginine at amino acid 505 of the VP1 of AAVrh74. In some aspect, other amino acids in the peptide are modified but this substitution is maintained. In some embodiments, the modification targets a receptor found primarily on satellite cells, optionally muscle stem cells. In some embodiments, the modification is an insertion of the peptide YIG or YIGSR (SEQ ID NO: 2) at amino acid position 591 of the VP1 of AAVrh74. In some aspect, other amino acids in the peptide are modified but this substitution is maintained. In some embodiments, this peptide has a has a high affinity for Alpha 7 beta 1 integrin and/or is positioned in a region that is likely to alter normal rh74 receptor binding. In some embodiments, the viral particle comprises one or more polynucleotides, and at least one of the polynucleotides comprises or consists essentially of, or yet further consists of a polynucleotide encoding a guide RNA (gRNA). In some aspects, at least one of the polynucleotides comprises or alternatively consists essentially of, or yet further consists of a therapeutic polypeptide. In some embodiments, the viral particle comprises a Cas9 or an equivalent thereof.

Provided herein is a non-human transgenic animal comprising a recombinant viral capsid particle comprising or alternatively consisting essentially of, or yet further consisting of a recombinant viral particle comprising or alternatively consisting essentially of a modified capsid wherein the modified capsid comprises a modified viral capsid protein comprising or alternatively consisting essentially of, or yet further consisting of modified viral capsid protein modified by amino acid substitution or insertion of between 1 to 7 amino acid. In some embodiments, viral capsid protein is a VP1, optionally of AAVrh74. In some aspect, other amino acids in the peptide are modified but this substitution is maintained. In further embodiments, the modification comprises the substitution of isoleucine for asparagine at amino acid position 502 of the VP1 of AAVrh74 or an equivalent modification. In some aspect, other amino acids in the peptide are modified but this substitution is maintained. In some embodiments, the modification comprises the substitution of tryptophan to arginine at amino acid 505 of the VP1 of AAVrh74. In some aspect, other amino acids in the peptide are modified but this substitution is maintained. In some embodiments, the modification targets a receptor found primarily on satellite cells, optionally muscle stem cells. In some embodiments, the modification is an insertion of the peptide YIG or YIGSR (SEQ ID NO: 2) at amino acid position 591 of the VP1 of AAVrh74. In some aspect, other amino acids in the peptide are modified but this substitution is maintained. In some embodiments, this peptide has a has a high affinity for Alpha 7 beta 1 integrin and/or is positioned in a region that is likely to alter normal rh74 receptor binding.

In some aspects, the polynucleotide encoding the gRNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and trans-activating CRIPSPR RNA (tracrRNA). In some aspects, the gRNA is specific for a region of DNA that is in need of gene editing in the subject or cell in need thereof.

In some aspects, the recombinant viral particle further comprising a therapeutic polynucleotide. The therapeutic polynucleotide is any polypeptide that can be used to target a DNA sequence in need of editing, provide a repair template for a DNA sequence in need of editing, or provide a replacement for a DNA sequence in need of editing. In further aspects, the therapeutic polypeptide comprises a wild-type sequence of a gene in need of editing in the subject or cell in need thereof.

Still further aspects relate to methods of treating a subject having a disease, disorder, or condition comprising administering the modified AAV disclosed herein to the subject. In some aspects, the disease, disorder, or condition is selected from the group of hemophilia, muscular dystrophy, multiple sclerosis, alpha-1-antitrypsin, amyotrophic lateral sclerosis, Alzheimer's, spinal muscular atrophy, cystic fibrosis, HIV, thalassemia, choroideremia, Parkinson's, Leber congenital amaurosis, macular degeneration, aromatic amino acid decarboxylase deficiency, achromatopsia, Crigler Najjar syndrome, Pompe disease, X-linked retinoschisis, homozygous familial hypercholesteremia, Batten disease, retinal degeneration, ornithine transcarbamylase deficiency, mucopolysarccharidosis (I-IX), hepatitis B, and hepatitis C. In one aspect, the hemophilia is characterized by one or more of factor VIII or factor IX deficiency. In some aspects, the muscular dystrophy is selected from Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

In some aspects, guide RNA and/or the therapeutic polynucleotide is designed and/or selected to treat a disease, disorder, or condition selected from the group of hemophilia, muscular dystrophy, multiple sclerosis, alpha-1-antitrypsin, amyotrophic lateral sclerosis, Alzheimer's, spinal muscular atrophy, cystic fibrosis, HIV, thalassemia, choroideremia, Parkinson's, Leber congenital amaurosis, macular degeneration, aromatic amino acid decarboxylase deficiency, achromatopsia, Crigler Najjar syndrome, Pompe disease, X-linked retinoschisis, homozygous familial hypercholesteremia, Batten disease, retinal degeneration, ornithine transcarbamylase deficiency, mucopolysarccharidosis (I-IX), hepatitis B, and hepatitis C. In one aspect, the hemophilia is characterized by one or more of factor VIII or factor IX deficiency. In some aspects, the muscular dystrophy is selected from Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

Figure 4:
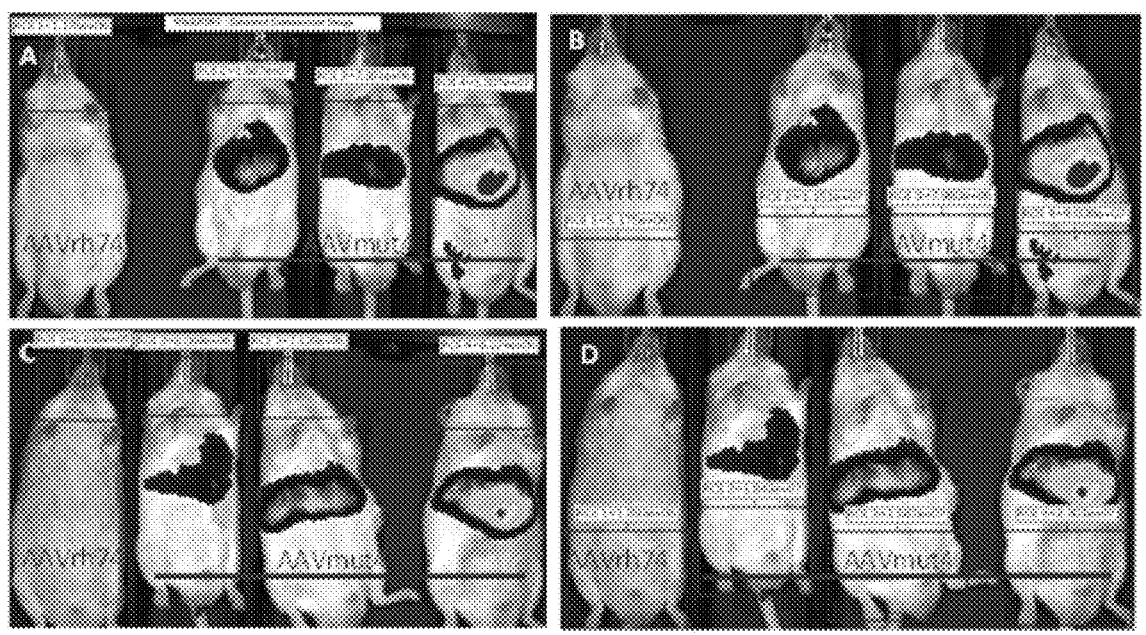
FIG. 4 shows live animal imaging of AAVmut4 and mut5 luminescence. Adult CD-1 mice were injected via the tail vein with 1E+11 Vg of either AAVrh74 or AAVmut4 virus containing the same luciferase vector. Mice were imaged 3 weeks post injection for luciferase expression. Two separate experiments were performed under the same conditions. Exp. 1, same animals in A and B with either head quantification of photons A, or leg quantification of photons, B. Exp. 2 is repeat of Exp. 1 with separate animals done 4 weeks later. Left most animal of each group of 4 is injected with AAVrh74 control virus, next 3 animals of each group are injected with AAVmut4 virus.
Figure 5:
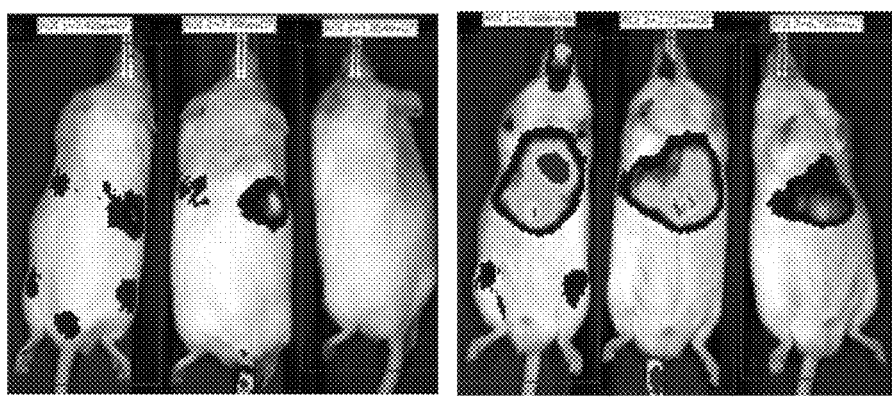
FIG. 5 shows live animal imaging of AAVYIG or AAVYIGSR591 luminescence. Adult CD-1 mice were injected via the tail vein with 1E+11 Vg of AAVYIG or AAVYIGSR591 virus containing the luciferase vector. Mice were imaged 3 weeks post injection for luciferase expression with whole body photon counts shown above each mouse in either ventral or dorsal position.

In some aspects, the guide RNA and/or the therapeutic polynucleotide is designed and/or selected to target or repair a gene selected from the group of Factor VIII (F8, NM_000132, NM_019863), Factor IX (F9, NM_000133, NM_001313913), dystrophin (DMD, NM_000109, NM_004006, NM_004007, NM_004009, NM_004010), dysferlin (DYSF, NM_001130455, NM_001130976, NM_001130977, NM_001130978, NM_001130979), emerin (EMD, NM_000117), lamin A/C (LMNA, NM_001257374, NM_001282624, NM_001282625, NM_001282626, NM_005572), double homeobox 4 (DUX4, NM_001205218, NM_001278056, NM_001293798, NM_001306068), myotonin-protein kinase (MDPK, NM_001081560, NM_001081562, NM_001081563, NM_001288764, NM_001288765), cellular nucleic acid-binding protein (CNBP, NM_003418, NM_001127192, NM_001127193, NM_001127194, NM_001127195), polyadenylate-binding protein-2 (PABP-2, NM_004643), Alpha-1-antitrypsin, superoxide dismutase (SOD1, NM_000454), alsin (ALS2, NM_001135745, NM_020919), helicase senataxin (SETX, NM_015046), spatacsin (SPG11, NM_001160227, NM_025137), RNA-binding protein FUS/TLS (FUS, NM_001010850, NM_001170634, NM_001170937, NM_004960), Vesicle-associated membrane protein-associated protein B/C (VAPB, NM_001195677, NM_004738), angiogenin (ANG, NM_001145, NM_001097577), TAR DNA-binding protein 43 (TARDBP, NM_007375), Polyphosphoinositide phosphatase (FIG4, NM_014845), optineurin (OPTN, NM_001008211, NM_001008212, NM_001008213, NM_021980), ataxin-2 (ATXN2, NP_001297050, NP_001297052, NP_002964), valosin-containing protein (VCP, NM_007126), ubiquilin-2 (UBQLN2, NM_013444), sigma-1 receptor (SIGMAR1, NM_001282205, NM_001282206, NM_001282207, NM_001282208, NM_001282209), Charged multivesicular body protein 2b (CHMP2B, NM_001244644, NM_014043), profilin-1 (PFN1, NM_005022), Receptor tyrosine-protein kinase erbB-4 (ERBB4, NM_001042599, NM_005235), Heterogeneous nuclear ribonucleoprotein A1 (HNRNPA1, NM_002136, NM_031157), matrin-3 (MATR3, NM_199189, NM_001194954, NM_001194955, NM_001194956, NM_001282278), tubulin alpha-4A chain (TUBA4A, NM_001278552, NM_006000), chromosome 9 open reading frame 72 (C9orf72, NM_145005, NM_001256054, NM_018325), CHCD10, SQSTM1 (NM_001142298), TBK1, apolipoprotein E (NM_001302691, NM_000041, NM_001302688, NM_001302689, NM_001302690), SMN1 (NM_000344), SMN2 (NM_017411, NM_022875, NM_022876, NM_022877), CTFR (NM_000492), beta globin HBB PDB, CHM, alpha-synuclein (SNCA, NM_000345), parkin (PRKN, NM_004562), leucine-rich repeat kinase 2 (LRRK2 or dardarin, NM_198578), PTEN-induced putative kinase 1 (PINK1, NM_032409), DJ-1 (NM_001123377), acid maltase (NM_000152), UDP-glucuronosyltransferase 1 (NM_000463), PPT-1 (NM_000310), or ATP13A2 (NM_001141973).

Additional aspects of the invention relate to compositions comprising a carrier and the modified virus described herein. Briefly, pharmaceutical compositions of the present invention may comprise the modified viral particle described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

It is appreciated by those skilled in the art that gRNAs can be generated for target specificity to target a specific gene, optionally a gene associated with a disease, disorder, or condition. Thus, in combination with Cas9, the guide RNAs facilitate the target specificity of the CRISPR/Cas9 system. Further aspects such as promoter choice, as discussed above, may provide additional mechanisms of achieving target specificity—e.g., selecting a promoter for the guide RNA encoding polynucleotide that facilitates expression in a particular organ or tissue. Accordingly, the selection of suitable gRNAs for the particular disease, disorder, or condition is contemplated herein.

Administration of the modified AAV or compositions can be effected in one dose, continuously or intermittently throughout the course of treatment. Administration may be through any suitable mode of administration, including but not limited to: intravenous, intra-arterial, intramuscular, intracardiac, intrathecal, subventricular, epidural, intracerebral, intracerebroventricular, sub-retinal, intravitreal, intraarticular, intraocular, intraperitoneal, intrauterine, intradermal, subcutaneous, transdermal, transmuccosal, and inhalation.

Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. It is noted that dosage may be impacted by the route of administration. Suitable dosage formulations and methods of administering the agents are known in the art. Non-limiting examples of such suitable dosages may be as low as 1E+9 vector genomes to as much as 1E+17 vector genomes per administration.

In a further aspect, the modified viral particle and compositions of the invention can be administered in combination with other treatments, e.g., those approved treatments suitable for the particular disease, disorder, or condition. A non-limiting example includes the treatment of muscular dystrophy with a combination of the modified viral particle and one or more steroids. One can determine if the treatment has been successful by monitoring for clinical or sub-clinical evidence of gene modification, as determined by the treating physician.

This administration of the modified viral particle or compositions of the invention can be done to generate an animal model of the desired disease, disorder, or condition for experimental and screening assays.

Modified AAV Capsids and Particles

The present disclosure provides also provides a specific embodiment, e.g., a modified adeno-associated virus (AAV) comprising a recombinant viral particle comprising or alternatively consisting essentially of a modified capsid wherein the modified capsid comprises a modified viral capsid protein comprising or alternatively consisting essentially of, or yet further consisting of modified viral capsid protein modified by amino acid substitution or insertion of between 1 to 7 amino acid. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In some aspect, other amino acids in the peptide are modified but this substitution is maintained. In some embodiments, the modification comprises the substitution of tryptophan to arginine at amino acid 505 of the VP1 of AAVrh74. In some aspect, other amino acids in the peptide are modified but this substitution is maintained. In some embodiments, the modification targets a receptor found primarily on satellite cells, optionally muscle stem cells. In some embodiments, the modification is an insertion of the peptide YIG or YIGSR (SEQ ID NO: 2) at amino acid position 591 of the VP1 of AAVrh74. In some aspect, other amino acids in the peptide are modified but this substitution is maintained. In some embodiments, this peptide has a has a high affinity for Alpha 7 beta 1 integrin and/or is positioned in a region that is likely to alter normal rh74 receptor binding.

Adeno-associated virus (AAV) vectors are replication defective viruses that are engineered to deliver genetic cargo efficiently to cells. They are non-enveloped viruses that in their vector form only possess the inverted terminal repeats (ITR) of the original virus. The structural and enzymatic AAV proteins are supplied "in trans" by additional plasmids and are transfected together into a cell to generate the engineered particles for gene delivery. AAVs have been widely utilized for genetic therapy—and more specifically with CRISPR/Cas9 systems—due to their safety and efficiency. AAV efficiently infects a variety of cells and during the infection process the capsid binds to and enters the nucleus where the vector genome is delivered.

The AAV structural particle is composed of 60 protein molecules made up of VP1, VP2 and VP3. Each particle contains approximately 5 VP1 proteins, 5 VP2 proteins and 50 VP3 proteins ordered into an icosahedral structure. It has been shown that AAV2 particles can support the insertion of peptides and proteins at various sites within the capsid structure. The ability to introduce unique peptides into the capsid has led to the development of AAV particles with altered tropism, which allows the virus to bind and infect cells and tissues that may normally be refractory to infection. In addition, large peptides and even functional proteins have been introduced into the capsid of AAV2 vectors with varying levels of success. A functional green fluorescent protein (GFP, 30 kD MW) containing AAV capsid was generated and produced infectious virus that was used to track cell infections.

One of the constraints with AAV vectors for gene delivery is the size limitation of the genetic insert that can be efficiently packaged into particles. For example, the size of the wild-type AAV2 genome is 4679 bases of single stranded DNA. Packaging even one of the new smaller variants of Cas9 (*Staphylococcus aureus* Cas9, SaCas9, 130 kD MW) requires approximately 3255 bp just for the coding region. Adding a ubiquitous or tissue specific promoter to the construct may add another 500-800 bp. Include another 500 bp for a poly A addition sequence and the ITR's and the vector is close to the packaging capacity of an AAV particle. To achieve functional CRISPR/Cas9 gene correction a guide RNA (gRNA) with the target sequence must also be included. To have this RNA expressed further requires a minimal polIII promoter and termination sequence. Together these elements are too large to be combined into an AAV vector that is efficiently packaged. One can choose to package the Cas9 construct and guide RNA expression cassettes into separate vectors, but, for them to be functional, both viruses must infect the same target cells.

Further aspects of the disclosure relate to a recombinant expression system for the generation of such a modified AAV. In some embodiments the recombinant expression system comprises a plurality of plasmids; the plurality encoding all of the AAV viral proteins—VP1, VP2, and VP3. In some embodiments, each viral protein is encoded in a different plasmid. In some embodiments, one or more viral proteins is encoded in the same plasmid. In some embodiments, at least one viral protein is encoded as a fusion protein with Cas9.

Accordingly, embodiments disclosed herein relate to a recombinant expression system for the generation of a modified AAV comprising a modified capsid wherein the modified capsid comprises a modified viral capsid protein comprising or alternatively consisting essentially of, or yet further consisting of modified viral capsid protein modified by amino acid substitution or insertion of between 1 to 7 amino acid. In some embodiments, viral capsid protein is a VP1, optionally of AAVrh74. In further embodiments, the modification comprises the substitution of isoleucine for asparagine at amino acid position 502 of the VP1 of AAVrh74 or an equivalent modification. In some aspect, other amino acids in the peptide are modified but this substitution is maintained. In some embodiments, the modification comprises the substitution of tryptophan to arginine at amino acid 505 of the VP1 of AAVrh74. In some aspect, other amino acids in the peptide are modified but this substitution is maintained. In some embodiments, the modification targets a receptor found primarily on satellite cells, optionally muscle stem cells.

Some aspects relate to methods of producing the modified AAVs using the recombinant expression system disclosed herein.

Still further aspects relate to methods of treating a subject having a disease, disorder, or condition comprising administering the modified AAV disclosed herein to the subject. In some embodiments, the disease, disorder, or condition is selected from the group of hemophilia, muscular dystrophy, multiple sclerosis, alpha-1-antitrypsin, amyotrophic lateral sclerosis, Alzheimer's, spinal muscular atrophy, cystic fibrosis, HIV, thalassemia, choroideremia, Parkinson's, Leber congenital amaurosis, macular degeneration, aromatic amino acid decarboxylase deficiency, achromatopsia, Crigler Najjar syndrome, Pompe disease, X-linked retinoschisis, homozygous familial hypercholesteremia, Batten disease, retinal degeneration, ornithine transcarbamylase deficiency, mucopolysarccharidosis (I-IX), hepatitis B, and hepatitis C. In some embodiments, the hemophilia is characterized by one or more of factor VIII or factor IX deficiency. In some embodiments, the muscular dystrophy is selected from Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

EXAMPLES

The following examples are non-limiting and illustrative of procedures which can be used in various instances in carrying the disclosure into effect. Additionally, all references disclosed herein below are incorporated by reference in their entirety.

AAVrh74 is a serotype of AAV identified by investigators at NCH that has been used extensively in clinical trials for the treatment of neuromuscular diseases. It efficiently infects human cardiac and skeletal muscles, and there is a low prevalence of pre-existing neutralizing antibodies in the human population.

Example 1—Determine the Optimal Modified Serotype for Maximal Myoblast and Satellite Cell Biodistribution by Vascular Delivery Muscle satellite cells are 60 times more abundant than muscle fiber cells in skeletal muscle [2]. They are a self-renewing stem cell population that facilitates the long-term regenerative capacity of skeletal muscle [12]. Recently several FACS-sortable markers have been identified for the isolation of muscle stem cells [13](FIG. 2). Alpha 7 beta 1 integrin has been identified as a positive muscle stem cell selection marker and is also the primary laminin receptor on skeletal myoblasts and adult myofibers. Expression studies have shown that alpha 7 beta 1 integrin is abundantly expressed on heart and skeletal muscle tissue and only low levels are found in liver tissue. Applicant has modified the AAVrh74 capsid to express a peptide that has been shown to bind with high affinity to alpha 7 beta 1 integrin protein. Applicant has positioned the peptide in a region that is likely to alter the normal AAVrh74 receptor binding motif in order to utilize β7β1-integrin as the binding receptor. Two additional mutations in other amino acids of AAVrh74 that are hypothesized to be necessary for liver specific binding and entry were also identified and shown to enable increased overall and/or muscle specific delivery of reporter genes after intravenous injection of vector (FIGS. 3-5).

C57BL/6J mice were intravenously injected with the newly created modified capsid viruses or control AAVrh74 (AAVmut4, AAVmut5 and AAVYIG or YIGSR591) expressing the same luciferase-EYFP fusion protein as previously demonstrated and after 3 weeks, the mice were sacrificed with PBS/paraformaldehyde perfusion followed by immunohistochemical staining of the sectioned muscles and organs to determine the specific cell populations that are transduced. Initially, the mice are imaged weekly for luciferase expression using the IVIS imaging system to confirm gene expression. Three-weeks post-injection, the mice are perfused, tissues will be harvested and fixed in paraformaldehyde, followed by sectioning and staining for GFP expression by immunofluorescence and counterstained for expression of cell type specific antigens for identification. This approach enabled Applicant to identify the specific cell populations transduced by the different capsid mutant vectors to determine which will likely have the most benefit for the muscle disease targeted.

AAVrh74 is the current standard for high level gene expression in skeletal and cardiac muscles and was used as the backbone for capsid modifications. Vector biodistribution after intravenous injection of CD-1 mice was determined by qPCR three weeks post-injection of the control and three capsid modified viruses (FIG. 3). The mut4 vector showed an overall increased global biodistribution of vector with significant increases in quadriceps, diaphragm and heart muscle. Whereas, mut5 and YIG or YIGSR591 showed significantly increased vector transduction of heart over AAVrh74.

TABLE 1

| Tissue | Mut4 Fold change above AAVrh74 |
|---|---|
| Blood | 18 |
| Brain | 8 |
| Lung | 5 |
| Quad | 10 |
| Diaphragm | 17 |
| Heart | 11 |
| Spleen | 3 |
| Kidney | 8 |
| Liver | 56 |

FIGS. 4 and 5 show enhanced in vivo expression of the mut4 and YIG or YIGSR591 delivered luciferase gene over parental AAVrh74. FIG. 4 shows the increased photon counts in either the head region or lower torso bracketed to show the effectiveness of the mut4 virus in transduction and gene expression in a wide variety of tissues.

Inbred C57BL/6J mice (6 per virus group, 3 male and 3 female) are used to confirm the previous biodistribution profile of the outbred CD-1 mice. The 4 viruses are prepared and ready to inject into mice upon arrival.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

REFERENCES

1. Fang, H., et al., Comparison of adeno-associated virus serotypes and delivery methods for cardiac gene transfer. Hum Gene Ther Methods, 2012. 23(4): p. 234-41.
2. Bianconi, E., et al., An estimation of the number of cells in the human body. Ann Hum Biol, 2013.40(6): p. 463-71.
3. Tran, T., et al., Laminin drives survival signals to promote a contractile smooth muscle phenotype and airway hyperreactivity. FASEB J, 2013. 27(10): p. 3991-4003.
4. Mori, S., et al., Biodistribution of a low dose of intravenously administered AAV-2, 10, and 11 vectors to cynomolgus monkeys. Jpn J Infect Dis, 2006. 59(5): p. 285-93.
5. Grimm, D., et al., In vitro and in vivo gene therapy vector evolution via multispecies interbreeding and retargeting of adeno-associated viruses. J Virol, 2008. 82(12): p. 5887-911.
6. Asokan, A., et al., Reengineering a receptor footprint of adeno-associated virus enables selective and systemic gene transfer to muscle. Nat Biotechnol, 2010. 28(1): p. 79-82.
7. Pulicherla, N., et al., Engineering liver-detargeted AAV9 vectors for cardiac and musculoskeletal gene transfer. Mol Ther, 2011. 19(6): p. 1070-8.
8. DiMattia, M. A., et al., Structural insight into the unique properties of adeno-associated virus serotype 9. J Virol, 2012. 86(12): p. 6947-58.
9. Li, C., et al., Single amino acid modification of adeno-associated virus capsid changes transduction and humoral immune profiles. J Virol, 2012. 86(15): p. 7752-9.
10. Raupp, C., et al., The threefold protrusions of adeno-associated virus type 8 are involved in cell surface targeting as well as postattachment processing. J Virol, 2012. 86(17): p. 9396-408.
11. Govindasamy, L., et al., Structural insights into adeno-associated virus serotype 5. J Virol, 2013. 87(20): p. 11187-99.
12. Bentzinger, C. F., et al., Cellular dynamics in the muscle satellite cell niche. EMBO Rep, 2013. 14(12): p. 1062-72.
13. Wang, Y. X., N. A. Dumont, and M. A. Rudnicki, Muscle stem cells at a glance. J Cell Sci, 2014. 127(21): p. 4543-8.
14. Loiler, S. A., et al., Targeting recombinant adeno-associated virus vectors to enhance gene transfer to pancreatic islets and liver. Gene Ther, 2003. 10(18): p. 1551-8.

What is claimed is:

1. A modified AAVrh74 VP1 capsid protein comprising one or more modifications selected from the group consisting of: a substitution of asparagine to isoleucine at amino acid position 502 of SEQ ID NO: 4, a substitution of tryptophan to arginine at amino acid position 505 of SEQ ID NO: 4, and an insertion of the peptide YIG or YIGSR (SEQ ID NO: 2) at amino acid position 591 of SEQ ID NO: 4.

2. A recombinant viral particle comprising the modified AAVrh74 VP1 of claim 1.

3. The recombinant viral particle of claim 2, further comprising a transgene or CRISPR system.

4. A polynucleotide encoding the modified AAVrh74 VP1 of claim 1.

5. A recombinant expression system for producing the recombinant viral particle of claim 2.

6. An isolated host cell comprising the polynucleotide of claim 4.

7. A kit comprising a recombinant viral particle that comprises the modified capsid protein of claim 1.

8. A polynucleotide encoding the recombinant viral particle of claim 2.

9. A vector comprising the polynucleotide of claim 8.

10. A recombinant expression system comprising the vector of claim 9 for producing the recombinant viral particle.

11. An isolated host cell comprising the vector of claim 9.

* * * * *